(12) United States Patent
Ng et al.

(10) Patent No.: US 6,790,445 B1
(45) Date of Patent: Sep. 14, 2004

(54) PRESERVATIVES FOR VACCINES

(75) Inventors: Assunta S. Ng, Lansdale, PA (US); Ralph J. Mancinelli, Harleysville, PA (US); John P. Hennessey, Dublin, PA (US)

(73) Assignee: Merck & Co., Inc., Rahway, NJ (US)

( * ) Notice: Subject to any disclaimer, the term of this patent is extended or adjusted under 35 U.S.C. 154(b) by 1143 days.

(21) Appl. No.: 09/019,764

(22) Filed: Feb. 6, 1998

Related U.S. Application Data

(60) Provisional application No. 60/036,900, filed on Feb. 6, 1997.

(51) Int. Cl.[7] .............................................. A61K 39/00
(52) U.S. Cl. ................................. 424/184.1; 424/189.1
(58) Field of Search ........................... 424/184.1, 189.1

(56) References Cited

U.S. PATENT DOCUMENTS

| | | | |
|---|---|---|---|
| 5,087,638 A | * | 2/1992 | Belanger et al. ............ 514/456 |
| 5,540,033 A | * | 7/1996 | Fox et al. ...................... 53/425 |
| 5,603,933 A | | 2/1997 | Dwyer, IV et al. |
| 5,643,605 A | * | 7/1997 | Cleland et al. ............. 424/489 |
| 5,672,350 A | | 9/1997 | Parker et al. |

FOREIGN PATENT DOCUMENTS

EP  0 750 907 A2  6/1996

OTHER PUBLICATIONS

Wallhausser, et al., Antimicrobial preservative in biologics:, Drugs Made in Germany, Dec. 1974, vol. 17, pp. 102–128.
Tracy, et al., "Preservatives for Poliomyelitis (Salk) Vaccine II", Journal of Pharmaceutical Sciences vol. 53, No. 6, Jun. 1964, pp. 659–663.
Lowe, I. et al.; The antimicrobial activity of phenoxyethanol in vaccines; Letters in Applied Microbiology; vol. 18; 1994; pp 115–116.
Kneczke, M.; Determination of pilocarpine, physostigmine, its degradation product rubreserine and preservatives by high–performance liquid chromatography; Journal of Chromatography; vol. 198; 1980; pp 529–533.
Monath, T.P.; Stability of Yellow Fever Vaccine; Dev Biol Stand. Basel, Karger; Vol 87; 1996; pp 219–225.
Cameron, J. Preservative Systems Compatible with DPTPolio (SALK) and TABTD–Polio (SALK) Vaccines; Develop. Biol. Standard; vol. 24; 1974 pp 155–165.

* cited by examiner

*Primary Examiner*—Sheela Huff
(74) *Attorney, Agent, or Firm*—Jack L. Tribble

(57) ABSTRACT

Novel combination of preservatives (methyl and propyl parabens, benzyl alcohol, and 2-phenoxyethanol) were found to pass antimicrobial testing according to USP, BP, and EP. The new preservatives were put into vaccines using L-histidine as a buffer to keep pH at 7.0. HPLC methods were developed to analyze these preservatives and their degradation products.

9 Claims, 2 Drawing Sheets

PRESERVATIVES FOR VACCINES

CROSS-REFERENCE TO RELATED APPLICATIONS

This application claims priority to provisional application No. 60/036,900, filed Feb. 6, 1997.

STATEMENT REGARDING FEDERALLY-SPONSORED R&D

Not applicable.

REFERENCE TO MICROFICHE APPENDIX

Not applicable.

FIELD OF THE INVENTION

The disclosure relates to thimerosal-free preservatives for vaccines.

BACKGROUND OF THE INVENTION

For multidose vaccine formulations, preservatives are required to prevent contamination of and to stabilize the composition of subsequent doses after the first dose is used. The preservative must enable the vaccine formulation to pass efficacy tests or antimicrobial challenge tests according to the United States Pharmacopeia (USP) in the U.S., British Pharmacopeia (BP), and European Pharmacopeia (EP) in Europe.

Thimerosal is a commonly-used preservative in vaccines. Thimerosal is a mercurial compound that is potentially toxic, and causes allergic reaction in about sixteen percent of the population. Thimerosal is also toxic to the environment.

It would be advantageous to find new and safer preservatives for vaccines to replace thimerosal. In this application, we report on new combinations of preservatives for vaccines: methyl and propyl parabens, benzyl alcohol, and 2-phenoxy-ethanol. These combination preservatives are non-toxic, yet effective.

One dose of vaccine (0.5 mL) has about 1 mg paraben. Toxicity of the parabens is relatively low, due to the ease and rapidity with which the body rids itself of these drugs. The $LD_{50}$ of methyl paraben in mice intraperitoneally is 1 g/kg.

One dose of vaccine has about 7.5 mg benzyl alcohol. This amount is below harmful levels. Benzyl alcohol is metabolized to benzoic acid, which is conjugated with glycine in the liver, and excreted as hippuric acid. The probable lethal dose of benzyl alcohol is 0.5–5.0 g/kg.

One dose of vaccine has 2 mcL of 2-phenoxyethanol. Toxicity of 2-phenoxyethanol is low. It has been in commercial use for several decades. The presence of 2-phenoxyethanol is known in volatile naturally occurring substances, such as green tea. The acute oral $LD_{50}$ in rats is 1.26–2.33 mL/kg. The acute dermal $LD_{50}$ in rabbits is 2.0 mL/kg.

Due to stringent antimicrobial requirements of the various pharmacopeias, finding the right preservative for vaccine formulations is a challenge. The pH of the vaccine should be maintained at approximately pH 7. pH also has an effect on the antimicrobial effectiveness of the preservatives. Solubility of some preservatives, such as the parabens, at pH 7 and at 4° C. is a limiting factor. Thus, the use of combination preservatives such as methyl and propyl parabens helps to solubilize more parabens. Each paraben has its own solubility for pH 7 and 4 degrees centigrade. Using both methyl and propyl parabens together rather than separately, helps to put more paraben in solution. Methyl paraben and propyl paraben work synergistically, since they exhibit differential antimicrobial activities.

The search for an effective buffer which maintains pH at pH 7 and which is safe for injectibles, is another challenge. Phosphate is the most commonly used buffer of choice for pH 7. However, phosphate buffer is incompatible with many forms of aluminum hydroxide adjuvant used in vaccine formulations. Other buffers effective at this pH range may not be safe for injectibles. In this application, we report the use of L-histidine, because it is an effective buffer at pH 7, and at 20–35 mM final concentration is safe to use in vaccines.

We have developed sample preparation and high performance liquid chromatography methods for analyzing these preservatives and their degradation products in vaccines. Methods for simultaneously analyzing some of these preservatives and their degradation products are not yet present in the literature.

SUMMARY OF THE INVENTION

New combinations of preservatives that pass antimicrobial testing requirements for United States Pharmacopeia (USP), British Pharmacopeia (BP), and European Pharmacopeia (EP). They are: (1) 1.5% benzyl alcohol; (2) 0.225% methyl paraben sodium, 0.025% propyl paraben sodium; and 0.9% benzyl alcohol, and (3) 0.225% methyl paraben sodium, 0.025% propyl paraben sodium, and 0.375% 2-phenoxyethanol. L-histidine is used as a buffer to keep pH of vaccines neutral. A new technique for analysis of combination preservatives and their degradation products in vaccines is also provided.

DETAILED DESCRIPTION OF THE INVENTION

Figure 1:
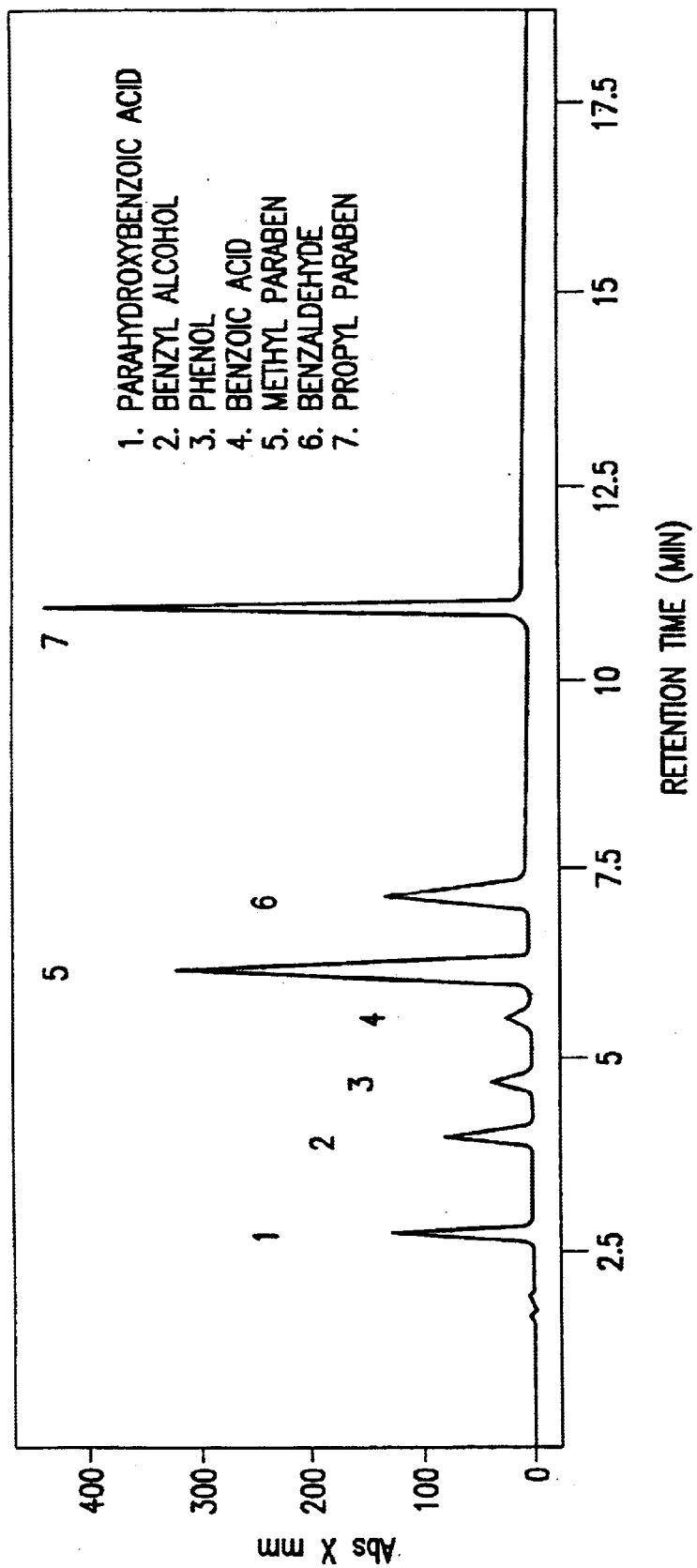
FIG. 1: Reversed-Phased HPLC Chromatogram of Preservative Related Components: (1) parahydroxybenzoic acid, (2) benzyl alcohol, (3) phenol, (4) benzoic acid, (5) methyl paraben, (6) benzaldehyde, and (7) propyl paraben.
Figure 2:
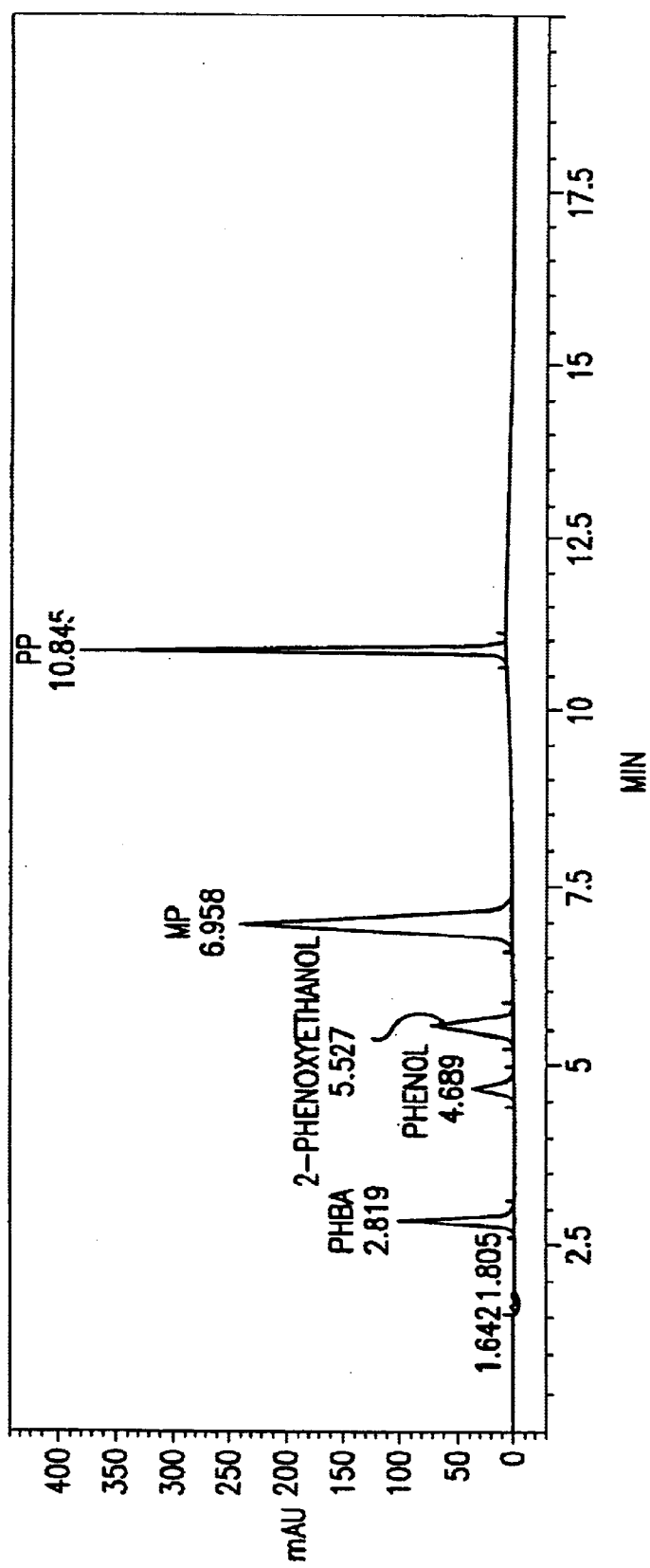
FIG. 2: HPLC Assay of Preservatives (Methyl Paraben, Propyl Paraben, 2-Phenoxyethanol, Benzyl Alcohol, and m-Cresol) in Vaccines.

Preservatives must pass antimicrobial efficacy tests. We performed the antimicrobial tests according to United States Pharmacopeia (USP), British Pharmacopeia (BP), and European Pharmocopeia (EP). Five test organisms were used: *Asperigillus niger, Candida albicans, Pseudomonas aeruginosa, Staphylococcus aureus*, and *Escherichia coli*. We have found new combinations of preservatives that passed antimicrobial testing. Three combinations passed all antimicrobial requirements for USP, BP, and EP. They are: (1) 1.5% benzyl alcohol, (2) 0.225% methyl paraben sodium, 0.025% propyl paraben sodium, and 0.9% benzyl alcohol, and (3) 0.225% methyl paraben sodium, 0.025% propyl paraben sodium, and 0.375% 2-phenoxyethanol. Five other preservative combinations passed USP, but failed BP, and EP. They are: (4) 0.18% methyl paraben sodium, plus 0.02% propyl paraben sodium, (5) 0.9% benzyl alcohol, (6) 0.18% methyl paraben sodium, plus 0.02% propyl paraben sodium, 25 ppm formaldehyde, (7) 0.18% methyl paraben sodium, plus 0.02% propyl paraben sodium, 0.5% benzyl alcohol, and (8) 0.27% methyl paraben sodium, plus 0.03% propyl paraben sodium.

EXAMPLE 1

Preparation of Vaccine Formulations

Vaccine formulations were prepared as follows. Preservatives were first prepared as concentrated stock solutions. Methyl paraben sodium is first dissolved in water at room temperature to 20% (w/v). (For example, weigh out 0.1 gm of methyl paraben sodium, and add 0.5 mL of water to make a stock of 20% solution.) Propyl paraben sodium is first dissolved in water at room temperature to 2% (w/v). (For example, weight out 0.03 gm of propyl paraben sodium, and add 1.5 mL of water to make a 2% solution.) 2-Phenoxyethanol is first dissolved in absolute ethanol to 50% (v/v). (For example, mix 1 mL of 2-Phenoxyethanol with 1 mL of water to give a 50% solution). Benzyl alcohol is used as is (v/v).

Two vaccines were studied. One is a hepatitis B vaccine, a yeast-derived recombinant hepatitis B surface antigen. The second is a combination vaccine, composed of hemophilized influenza type B, a yeast-derived recombinant hepatitis B surface antigen, diphtheria, tetanus, and acellular pertussis components. Hepatitis B vaccine is Thimerosal-free, Recombivax®HB, BAP (Hepatitis B surface antigen)=10 mcg/mL and 450 mcg aluminum hydroxide/mL.

L-histidine is used as a buffer to maintain pH 7. Buffer is added before addition of preservatives. For vaccines with parabens, L-histidine stock solution (0.5 M; pH 6) is added to vaccine.

The combination vaccine was designated as AR5. AR5 is composed of Recombivax®, 10 mcg/mL HBsAg (hepatitis B surface antigen), PRP-T (ActHib), 20 mcg PRP/mL, Agglutinogens, 10 mcg/mL, 69K (Pertactin), 6 mcg/mL, Filamentous Hemagglutinen, 40 mcg/mL, LPF (PT or Pertussis Toxoid), 40 mcg/mL, Diphtheria, 30 Lf/mL, and Tetanus, 10 Lf/mL, to a final concentration of 20–35 mM histidine. The sodium salts of parabens are at pH 9; thus using stock L-histidine buffer at pH 6 will maintain final pH at pH 7. (For example, to make 5 mL of vaccine with 0.225% methyl paraben sodium, 0.025% propyl paraben sodium, and 0.9% benzyl alcohol: to a glass vial, add 4496 mcL of vaccine, 90 mcL of water, 25 mcL of 0.5 M histidine solution, pH 6, 56 mcL of 20% methyl paraben, 63 mcL of 2% propyl paraben, and 45 mcL of benzyl alcohol. Mix to dissolve.)

EXAMPLE 2

To make 100 mL of AR5, add 50 mL of Recombivax®HB, 20 mcg/mL, mixed with 2.67 mL of CLL (aluminum hydroxide; 11 mL of PRP-T (ActHib), 181.5 mcgPRP/mL; 3.48 mL of Agglutinogens, 287 mcg/ml; 2.07 mL of 69K (Pertactin), 290 mcg/mL; 5.71 mL of Filamentous Humagglutinin, 700 mcg/mL; 11.05 mL of LPF (Pertussis Toxoid), 362 mcg/mL; 0.875 mL of Diphtheria, 3430 Lf/mL mixed with 8.00 mL aluminum hydroxide; and 0.379 mL of Tetanus, 2640 Lf/mL mixed with 2.67 mL aluminum hydroxide. For vaccines preserved with benzyl alcohol alone, L-histidine solution at 0.5 M, initial pH 7.0, is added to a final concentration of 20–35 mM. (For example, to make 5 mL of vaccine with 1.5% benzyl alcohol: to a glass vial, add 4496 mcL of vaccine, 33 mcL of 0.5 M histidine solution, pH 7, 97 mcL of water, and 75 mcL of benzyl alcohol. Mix to dissolve.) Add preservatives slowly, a little at a time, with slow stirring, so as not to chemically or physically alter vaccine components. Add parabens before benzyl alcohol or 2-phenoxethanol. The concentration of histidine is 20–35 mM. Final pH is 7. The final concentration of preservatives is as indicated in the formulation.

Preservatives are recovered by a first centrifugation to remove aluminum hydroxide adjuvant and proteins, and a second centrifugation through a 1000 molecular weight cutoff Millipore filter tube to remove all other formulation components. For example, pipette 200 mcL of vaccine with preservatives (0.225% methyl paraben sodium, 0.025% propyl paraben sodium, and 0.9% benzyl alcohol) into a 1.5 mL microcentrifuge tube. Centrifuge at maximum speed on table top microcentrifuge for 3 minutes at room temperature. Pipette out the supernatant into a clean microcentrifuge tube. Discard pellet. Pipette 40 mcL of supernatant and 160 mcL of water into a microfuge tube with 1000 molecular weight cutoff filter. Mix and centrifuge at maximum speed on table top microcentrifuge for 14 minutes at room temperature. 10 mcL of filtrate is injected into HPLC for analysis.

EXAMPLE 3

Preservatives such as methyl and propyl parabens, benzyl alcohol, benzoic acid, and phenol are routinely used for antimicrobial preservation in biological products. Quantitative analysis of methyl and propyl paraben by high performance liquid chromatography was popular. Quantitative analysis of methyl and propyl parabens and their degradation product, p-hydroxybenzoic acid has been carried out by thin layer chromatography (TLC) and high performance TLC. While benzyl alcohol and its degradation product, benzaldehyde, were analyzed using HPLC, other HPLC analyses of benzyl alcohol in pharmaceuticals were published. Analysis of phenol had been done by HPLC and GC.

In the course of our work, we developed a method for putting combination preservatives in biological products, facilitated by use of a buffering system for maintaining pH at 7. We also developed an efficient method of retrieving preservatives of interest for fast and accurate analysis by removing sample matrix interference. We also developed a simple HPLC method for the simultaneous separation of methyl and propyl parabens, parahydroxybenzoic acid, phenol, benzyl alcohol, benzaldehyde, and benzoic acid. Parahydroxybenzoic acid and phenol are degradation products of methyl and propyl parabens, while benzaldehyde and benzoic acid are degradation products of benzyl alcohol.

EXAMPLE 4

A Hewlett Packard HP 1090 Series HPLC consisting of autosampler, pump, and diode array detector was used. A variable wavelength detector is, however, sufficient for this work. The column was Waters_$\mu$-Bondapak C-18, RP column (30×3.9 mm I.D., 10 micrometer particles). The guard column used was also Waters-$\mu$-Bondapak. A Fisher Micro-Centrifuge Model 235A was used for centrifuging samples. A Millipore UF3 LGC WB 10,000 NMWL Filter unit was used for separating preservatives from possible sample matrix interference.

Acetonitrile was Omnisolve HPLC grade from EM Science. Benzaldehyde, benzoic acid, and phenol were from J. T. Baker. Benzyl alcohol was NF grade from A. A. Spectrum Chemical. Glacial acetic acid was Fisher Reagent ACS. L-histidine monochloride, monohydrate, was from Spectrum Chemical Mfg. Corp. Parabenzoic acid was from Sigma. Methyl paraben sodium was Nipagin M. Sodium, NF grade. Propyl paraben sodium was Nipasol M. Sodium, NF grade. Both were from Nippa Laboratories. Water was Milli-Q purified from in-house source.

EXAMPLE 5

Sample and Standard Preparation

The following method was used to add preservatives to the biological samples. Histidine solution at 100 mM stock, initial pH 6,0, was added as a buffer to a final concentration of 20 mM to keep the biological samples at pH 7.0 prior to addition of preservatives. Methyl and propyl parabens sodium were first dissolved in water at room temperature to 20% and 2% (w/v), respectively. Benzyl alcohol was used as is (v/v) without prior dilution. They were added to biological samples to the desired final concentrations. Standards were made fresh daily in the same manner using water instead of biological samples.

To separate the preservatives from the sample matrix for analysis, 200 ml of sample was centrifuged for 3 minutes at room temperature using the Fisher Micro-Centrifuge to remove insoluble materials. The supernatant obtained from the centrifugation was diluted with water to the desired target level, and then placed in a Millipore filter tube and centrifuged at room temperature for 14 minutes to remove additional sample matrix components. For analysis, 10 ml of filtrate was injected directly into the HPLC.

EXAMPLE 6

Quantitation of Preservative by HPLC

The mobile phase consisted of acetonitrile-water containing 2% (v/v) acetic acid with the following linear gradient of acetonitrile concentration: 0 min., 24%; 5 min., 24%; 9 min., 50%; 13 min., 24%. 10 ml of sample was injected. Flow rate was 2 mL/minute. Detector was set at 254 nm. Run time was 20 minutes and the assay was conducted at room temperature.

EXAMPLE 7

The sodium salts of methyl and propyl parabens were chosen instead of the esters, because the sodium salts are very soluble in water at room temperature. Histidine was used for these studies because histidine has effective buffering capacity near pH 7 (pKa=7 at 4° C.). Solutions of methyl and propyl parabens sodium have pH of about 9. To bring the pH to 7 with using only a final concentration of 20 mM histidine, an initial stock of 100 mM histidine, pH 6 was used.

After the preservatives were combined with the samples, the challenge was to quantitate the concentration of the preservatives with minimal interference from the sample matrix. This was achieved by centrifugation of the sample to remove insoluble components, followed by centrifugation through a 10K MW cutoff membrane. All preservatives studied passed through the filter membrane, with a recovery of better than 99%.

A chromatogram of the seven preservative-related components is shown in FIG. 1. Parahydroxybenzoic acid elutes as a peak with a retention time of 2.79 minutes, benzyl alcohol at 4.18 minutes, phenol at 5.14 minutes, benzoic acid at 6.07 minutes, methyl paraben at 6.91 minutes, benzaldehyde at 7.95 minutes, and propyl paraben at 11.21 minutes.

Table 1 shows the linearity, intercept, and slope for standard curves of all seven compounds. The calibration graphs were constructed from two injections each of five or more concentrations. The least square regression fit showed good linearity (R-square>0.999) in the defined range of the standard curve for all compounds.

TABLE 1

Linearity of Compounds

| Compound | Linear Range (mg) | Intercept | Slope | R-Square |
|---|---|---|---|---|
| benzaldhyde | 0.025–10.0 | 13.51 | 1844.1 | 0.999 |
| benzoic acid | 0.100–10.0 | 2.29 | 169.9 | 0.999 |
| benzyl alcohol | 0.500–7.5 | −0.31 | 49.3 | 0.999 |
| methyl paraben | 0.010–10.0 | 7.20 | 2469.0 | 0.999 |
| parahydroxy-benzoic acid | 0.100–2.5 | 36.59 | 2527.3 | 0.999 |
| phenol | 1.000–5.0 | −8.87 | 156.6 | 0.999 |
| propyl paraben | 0.500–5.0 | 41.22 | 2195.8 | 0.999 |

Table 2 shows the reproducibility of retention times for the seven compounds. Mean values were from six replicate injections. The relative standard deviations were better than 0.3% for the seven compounds.

TABLE 2

Reproducibility of Retention Times*

| Compound | Retention Time** (minutes) | R.S.D. (%) |
|---|---|---|
| parahydroxybenzoic acid | 2.79 | 0.25 |
| benzyl alcohol | 4.18 | 0.15 |
| phenol | 5.14 | 0.26 |
| benzoic acid | 6.07 | 0.28 |
| methyl paraben | 6.91 | 0.29 |
| benzaldehyde | 7.95 | 0.19 |
| propyl paraben | 11.21 | 0.05 |

*Chromatograph in FIG. 1
**Mean value of six replicates

Table 3 shows reproducibility of areas of six replicate injections. For six repeated injections in the same run, the relative standard deviations were better than 2% for all compounds. For between-day precision, seven spiked samples were analyzed in duplicate on seven separate days. The RSD (%) for methyl and propyl parabens was 5.4 and 15.1 respectively, and 8.4 for benzyl alcohol.

TABLE 3

Reproducibility of Areas*

| Compound | Area Units** | R.S.D. (%) |
|---|---|---|
| parahydroxybenzoic acid | 3080.5 | 0.1 |
| benzyl alcohol | 148.3 | 0.4 |
| phenol | 167.9 | 0.4 |
| benzoic acid | 197.6 | 0.4 |
| methyl paraben | 3453.0 | 0.1 |
| benzaldehyde | 1103.6 | 1.0 |
| propyl paraben | 359.8 | 2.0 |

*Chromatogram in FIG. 1
**Mean value of six replicate injections

Table 4 shows the limit of detection for each compound as measured by signal-to-noise ratio of 3:1.

TABLE 4

Limits of Detection and Quantitation

| Compound | LOD (ng) | LOQ (ng) |
|---|---|---|
| benzaldehyde | 25 | 25 |
| benzoic acid | 100 | 100 |
| benzyl alcohol | 250 | 500 |
| methyl paraben | 10 | 10 |
| parahydroxybenzoic acid | 10 | 100 |
| phenol | 100 | 1000 |
| propyl paraben | 25 | 500 |

Table 5 shows recovery studies of biological samples spiked with three different levels of preservatives. Recoveries were from 90 to 111%. As to specificity, we observed no interference from sample matrix components.

TABLE 5

Recovery Study of Preservatives in Biological Samples

| Compound | Amount Added % | Recovery* % | R.S.D.* |
|---|---|---|---|
| methyl paraben | 0.180 | 102 | 0.41 |
|  | 0.225 | 102 | 0.01 |
|  | 0.270 | 102 | 0.10 |
|  | 0.315 | 104 | 0.16 |
| propyl paraben | 0.020 | 90 | 0.46 |
|  | 0.025 | 97 | 0.42 |
|  | 0.030 | 96 | 0.14 |
| benzyl alcohol | 0.500 | 111 | 0.57 |
|  | 1.200 | 111 | 0.49 |
|  | 1.500 | 110 | 0.37 |
|  | 2.000 | 110 | 0.37 |

*Mean value of two repeated injections

EXAMPLE 8

Stability studies of the new preservative combinations in AR5 combination vaccine. AR5 is composed of Recombivax®HB, 10 mcg/mL, PRP-T (ActHib), 20 mcg/mL, Agglutinogens, 10 mcg/mL, 69K (Pertactin), 6 mcg/mL, Filamentous Hemagglutinen, 40 mcg/mL, LPF (PT or Pertussis Toxoid), 40 mcg/mL, Diphtheria, 30 Lf/mL, and Tetanus, 10 Lf/mL, and phosphate buffered saline, were done at 37° C. for 7, 12, 16, and 21 days and at 4° C. for 27, 57, and 96 days. There is no significant decrease in any of the preservatives concentration.

Table 6 shows stability studies of vaccine and phosphate buffered saline with 0.18% methyl paraben sodium, and 0.02% propyl paraben sodium. Samples for 37° C. were tested for 1, 7, 12, 16 and 21 days. Samples of 4° C. were tested for 1, 27, 28, 57 and 96 days. Amount of preservatives were compared to day 1.

TABLE 6

PERCENT PRESERVATIVES COMPARED TO DAY 1
0.18% METHYL PARABEN SODIUM,
PLUS 0.2% PROPYL PARABEN SODIUM

| Samples | Preservatives | | | | | |
|---|---|---|---|---|---|---|
|  | Day | 1 | 7 | 12 | 16 | 21 |
|  | Batch | 1 | 1 | 2 | 1 | 2 |
|  | Temperature C. |  | 37 | 37 | 37 | 37 |
| PBS | Methyl Paraben | 100 | 107 | 96 | 110 | 106 |
|  | Propyl Paraben | 100 | 104 | 88 | 96 | 99 |
| AR5 | Methyl Paraben | 100 | 116 | 101 | 122 | 126 |
|  | Propyl Paraben | 100 | 100 | 101 | 103 | 123 |
|  | Day | 1 | 27 | 28 | 57 | 96 |
|  | Batch | 1 | 1 | 2 | 1 | 2 |
|  | Temperature C. |  | 4 | 4 | 4 | 4 |
| PBS | Methyl Paraben | 100 | 103 | 107 | 107 | 118 |
|  | Propyl Paraben | 100 | 96 | 102 | 100 | 109 |
| AR5 | Methyl Paraben | 100 | 101 | 108 | 100 | 109 |
|  | Propyl Paraben | 100 | 87 | 109 | 87 | 107 |

PBS = Phosphate Buffered Saline
AR5 = Acthib, Recombivax, Diphtheria, Tetanus, and Pertussis acellular five components Table 7 is for 0.9% benzyl alcohol.

TABLE 7

PERCENT PRESERVATIVES COMPARED TO DAY 1
0.9% BENZYL ALCOHOL

| Samples | Preservatives | | | | | |
|---|---|---|---|---|---|---|
|  | Day | 1 | 7 | 12 | 16 | 21 |
|  | Batch | 1 | 1 | 2 | 1 | 2 |
|  | Temperature C. |  | 37 | 37 | 37 | 37 |
| PBS | Benzyl Alcohol | 100 | 120 | 100 | 141 | 128 |
| AR5 | Benzyl Alcohol | 100 | 83 | 81 | 82 | 70 |
|  | Day | 1 | 27 | 28 | 57 | 96 |
|  | Batch | 1 | 1 | 2 | 1 | 2 |
|  | Temperature C. |  | 4 | 4 | 4 | 4 |
| PBS | Benzyl Alcohol | 100 | 108 | 121 | 105 | 101 |
| AR5 | Benzyl Alcohol | 100 | 71 | 81 | 66 | 90 |

PBS = Phosphate Buffered Saline
AR5 = Acthib, Recombivax, Diphtheria, Tetanus, and Pertussis acellular 5 components Table 8 is for 0.6% phenoxyethanol.

TABLE 8

PERCENT PRESERVATIVES COMPARED TO DAY 1
0.6% PHENOXYETHANOL

| Samples | Preservatives | | | | | |
|---|---|---|---|---|---|---|
|  | Day | 1 | 7 | 12 | 16 | 21 |
|  | Batch | 1 | 1 | 2 | 1 | 2 |
|  | Temperature C. |  | 37 | 37 | 37 | 37 |
| PBS | Phenoxyethanol | 100 | 100 | 97 | 107 | 118 |
| AR5 | Phenoxyethanol | 100 | 88 | 81 | 106 | 87 |
|  | Day | 1 | 27 | 28 | 57 | 96 |
|  | Batch | 1 | 1 | 2 | 1 | 2 |
|  | Temperature C. |  | 4 | 4 | 4 | 4 |
| PBS | Phenoxyethanol | 100 | 96 | 115 | 101 | 130 |
| AR5 | Phenoxyethanol | 100 | 73 | 87 | 79 | 115 |

PBS = Phosphate Buffered Saline
AR5 = Acthib, Recombivax, Diphtheria, Tetanus, and Pertussis acellular 5 components Table 9 for 0.18% methyl paraben sodium, 0.02% propyl paraben sodium, and 0.25% phenoxyethanol.

TABLE 9

PERCENT PRESERVATIVES COMPARED TO DAY 1
0.18% METHYL PARABEN SODIUM,
0.2% PROPYL PARABEN SODIUM,
AND 0.25% 2-PHENOXYETHANOL

| Samples | Preservatives | | | | | |
|---|---|---|---|---|---|---|
| | Day | 1 | 7 | 12 | 16 | 21 |
| | Batch | 1 | 1 | 2 | 1 | 2 |
| | Temperature C. | | 37 | 37 | 37 | 37 |
| PBS | Methyl Paraben | 100 | 103 | 98 | 118 | 122 |
| | Propyl Paraben | 100 | 96 | 92 | 104 | 115 |
| | 2-Phenoxyethanol | 100 | 111 | 95 | 122 | 115 |
| AR5 | Methyl Paraben | 100 | 102 | 101 | 118 | 136 |
| | Propyl Paraben | 100 | 94 | 99 | 108 | 127 |
| | 2-Phenoxyethanol | 100 | 100 | 97 | 107 | 119 |
| | Day | 1 | 27 | 28 | 57 | 96 |
| | Batch | 1 | 1 | 2 | 1 | 2 |
| | Temperature C. | | 4 | 4 | 4 | 4 |
| PBS | Methyl Paraben | 100 | 102 | 108 | 102 | 121 |
| | Propyl Paraben | 100 | 92 | 105 | 91 | 112 |
| | 2-Phenoxyethanol | 100 | 108 | 106 | 105 | 100 |
| AR5 | Methyl Paraben | 100 | 100 | 104 | 99 | 95 |
| | Propyl Paraben | 100 | 93 | 108 | 91 | 95 |
| | 2-Phenoxyethanol | 100 | 99 | 102 | 95 | 77 |

PBS = Phosphate Buffered Saline
AR5 = Acthib, Recombivax, Diphtheria, Tetanus, and Pertussis acellular 5 components Table 10 for 0.18% methyl paraben sodium, 0.2% propyl paraben sodium, and 25 ppm formaldehyde.

TABLE 10

PERCENT PRESERVATIVES COMPARED TO DAY 1
0.18% METHYL PARABEN SODIUM, 0.2% PROPYL PARABEN
SODIUM, AND 25 PPM FORMALDEHYDE

| Samples | Preservatives | | | | | |
|---|---|---|---|---|---|---|
| | Day | 1 | 7 | 12 | 16 | 21 |
| | Batch | 1 | 1 | 2 | 1 | 2 |
| | Temperature C. | | 37 | 37 | 37 | 37 |
| PBS | Methyl Paraben | 100 | 104 | 140 | 118 | |
| | Propyl Paraben | 100 | 91 | 128 | 94 | |
| AR5 | Methyl Paraben | 100 | 105 | 102 | 118 | 119 |
| | Propyl Paraben | 100 | 96 | 101 | 109 | 114 |
| | Day | 1 | 27 | 28 | 57 | 96 |
| | Batch | 1 | 1 | 2 | 1 | 2 |
| | Temperature C. | | 4 | 4 | 4 | 4 |
| PBS | Methyl Paraben | 100 | 103 | 105 | 103 | 105 |
| | Propyl Paraben | 100 | 86 | 98 | 87 | 89 |
| AR5 | Methyl Paraben | 100 | 103 | 106 | 102 | 107 |
| | Propyl Paraben | 100 | 97 | 107 | 95 | 107 |

PBS = Phosphate Buffered Saline
AR5 = Acthib, Recombivax, Diphtheria, Tetanus, and Pertussis acellular 5 components Table 11 for 0.18% methyl paraben sodium, 0.2% propyl paraben sodium, and 0.5% benzyl alcohol. There was no significant decrease in concentration of any of the preservatives.

TABLE 11

PERCENT PRESERVATIVES COMPARED TO DAY 1
0.18% METHYL PARABEN SODIUM, 0.2% PROPYL PARABEN
SODIUM, AND 0.5% BENZYL ALCOHOL

| Samples | Preservatives | | | | | |
|---|---|---|---|---|---|---|
| | Day | 1 | 7 | 12 | 16 | 21 |
| | Batch | 1 | 1 | 2 | 1 | 2 |
| | Temperature C. | | 37 | 37 | 37 | 37 |
| PBS | Methyl Paraben | 100 | 104 | 104 | 108 | 112 |
| | Propyl Paraben | 100 | 91 | 94 | 89 | 101 |
| | Benzyl Alcohol | 100 | 107 | 103 | 105 | 103 |
| AR5 | Methyl Paraben | 100 | 105 | 101 | 126 | 123 |
| | Propyl Paraben | 100 | 96 | 99 | 115 | 118 |
| | Benzyl Alcohol | 100 | 96 | 98 | 102 | 109 |
| | Day | 1 | 27 | 28 | 57 | 96 |
| | Batch | 1 | 1 | 2 | 1 | 2 |
| | Temperature C. | | 4 | 4 | 4 | 4 |
| PBS | Methyl Paraben | 100 | 105 | 105 | 106 | 115 |
| | Propyl Paraben | 100 | 89 | 99 | 89 | 93 |
| | Benzyl Alcohol | 100 | 105 | 100 | 106 | 99 |
| AR5 | Methyl Paraben | 100 | 98 | 105 | 100 | 104 |
| | Propyl Paraben | 100 | 89 | 105 | 93 | 91 |
| | Benzyl Alcohol | 100 | 92 | 101 | 93 | 89 |

PBS = Phosphate Buffered Saline
AR5 = Acthib, Recombivax, Diphtheria, Tetanus, and Pertussis acellular 5 components

What is claimed:

1. A method of preserving vaccines comprising mixing vaccine solutions with a non-mercurial preservative to form a mixture of vaccine solution and preservative where the preservative and its final concentration in the mixture of vaccine solution and preservative is selected from the group consisting of:

(a) approximately 1.5% benzyl alcohol;

(b) approximately 0.225% methyl paraben sodium, approximately 0.025% propyl paraben sodium, and approximately 0.9% benzyl alcohol; and (c) approximately 0.225% methyl paraben sodium, approximately 0.025% propyl paraben sodium, and approximately 0.375% 2-phenoxyethanol.

2. Vaccines prepared by the method of claim 1.

3. The method of claim 1 where the vaccine solution is a combination vaccine, containing more than one antigen.

4. Vaccines prepared by the method of claim 3.

5. The method of claim 1 where the mixture of vaccine solution and preservative further comprises L-histidine buffer.

6. The method of claim 5 where the final concentration of L-histidine in the mixture of vaccine solution and preservative is about 20–35 mM.

7. The method of claim 5 where the vaccine solution is a combination vaccine, containing more than one antigen.

8. Vaccines prepared by the method of claim 5.

9. Vaccines prepared by the method of claim 7.

* * * * *